United States Patent [19]

Drewes et al.

[11] Patent Number: 5,981,436
[45] Date of Patent: Nov. 9, 1999

[54] SUBSTITUTED DIAZACYCLOHEXANEDI (THI) ONES

[75] Inventors: Mark-Wilhelm Drewes; Roland Andree, both of Langenfeld; Otto Schallner, Monheim; Hans-Joachim Santel; Markus Dollinger, both of Leverkusen, all of Germany

[73] Assignee: Bayer Aktiengesellschaft, Leverkusen, Germany

[21] Appl. No.: 09/069,475

[22] Filed: Apr. 29, 1998

Related U.S. Application Data

[62] Division of application No. 08/737,573, filed as application No. PCT/EP95/01700, May 5, 1995, abandoned.

[30] Foreign Application Priority Data

May 18, 1994 [DE] Germany ............................. 44 17 352
Jan. 4, 1995 [DE] Germany ........................... 195 00 118

[51] Int. Cl.⁶ .................. A01N 43/54; C07D 239/22; C07D 239/54; C07D 239/56
[52] U.S. Cl. .................. 504/243; 504/221; 504/223; 504/225; 544/50; 544/52; 544/92; 544/105; 544/310; 544/311; 544/312
[58] Field of Search ...................... 504/243, 221, 504/223, 225; 514/269; 544/311, 50, 310, 52, 312, 92, 105

[56] References Cited

U.S. PATENT DOCUMENTS 4,859,229  8/1989  Wenger et al. .................... 544/309
4,927,451  5/1990  Brower et al. .................... 544/309
5,356,863  10/1994 Satow et al. ..................... 544/310

FOREIGN PATENT DOCUMENTS 0 162 669   11/1985  European Pat. Off. .
42 06 416    9/1993  Germany .
WO 92/11244  7/1992  WIPO .

OTHER PUBLICATIONS

CA 120: 54550, 1993.
Chemical Abstracts, vol. 121, No. 11, 1994, Abstract No. 127858h, p. 389 (w/English Abstract).

Primary Examiner—Mukund J. Shah
Assistant Examiner—Deepak R. Rao
Attorney, Agent, or Firm—Sprung Kramer Schaefer & Briscoe

[57] ABSTRACT

The invention relates to new substituted diazacyclohexanedi (thi)ones of the general formula (I)

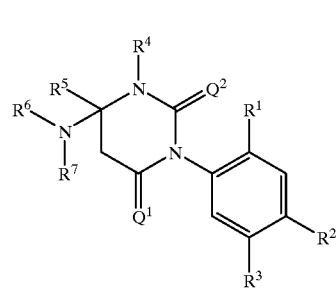

(I)

in which $Q^1$, $Q^2$, $R^1$, $R^2$, $R^3$, $R^4$, $R^5$, $R^6$ and $R^7$ have the meanings given in the description, a process for their preparation, new intermediate products and their use as herbicides.

4 Claims, No Drawings

SUBSTITUTED DIAZACYCLOHEXANEDI (THI) ONES

This application is a division of U.S. Ser. No. 08/737,573, filed Nov. 12, 1996 (now pending), which is a 371 of PCT/EP95/01700 filed May 5, 1995.

The invention relates to new substituted diazacyclohexanedi(thi)ones, a process for their preparation and their use as herbicides.

It is known that certain diazacyclohexanedi(thi)ones have herbicidal properties (cf. U.S. Pat. No. 4,927,451 and JP 06092943). However, the compounds known from the patent publications mentioned have not acquired noticeable importance.

The new diazacyclohexanedi(thi)ones of the general formula (I)

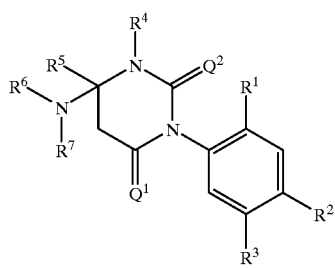

(I)

in which
- $Q^1$ represents oxygen or sulphur,
- $Q^2$ represents oxygen or sulphur,
- $R^1$ represents hydrogen, cyano, nitro or halogen, or represents in each case optionally halogen-substituted alkyl or alkoxy,
- $R^2$ represents hydrogen, cyano, nitro, thiocarbamoyl or halogen, or represents in each case optionally halogen-substituted alkyl or alkoxy,
- $R^3$ represents the following grouping $—A^1—A^2—A^3$ wherein
  - $A^1$ represents a single bond, or represents oxygen, sulphur, —SO—, —SO$_2$—, —CO— or the grouping —N—$A^4$—, wherein $A^4$ represents hydrogen, hydroxyl, alkyl, alkoxy, aryl, alkylsulphonyl or arylsulphonyl,
  - $A^1$ furthermore represents in each case optionally substituted alkanediyl, alkenediyl, azaalkenediyl, alkinediyl, cycloalkanediyl, cycloalkenediyl or arenediyl,
  - $A^2$ represents a single bond, or represents oxygen, sulphur, —SO—, —SO$_2$—, —CO— or the grouping —N—$A^4$—, wherein $A^4$ represents hydrogen, alkyl, aryl, alkylcarbonyl, alkylsulphonyl or arylsulphonyl,
  - $A^2$ futhermore represents in each case optionally substituted alkanediyl, alkenediyl, azaalkenediyl, alkinediyl, cycloalkanediyl, cycloalkenediyl or arenediyl and
  - $A^3$ represents hydrogen, hydroxyl, mercapto, amino, cyano, isocyano, thiocyanato, nitro, carboxyl, carbamoyl, thiocarbamoyl, sulpho, chlorosulphonyl or halogen, or represents in each case optionally substituted alkyl, alkoxy, alkylthio, alkylsulphinyl, alkylsulphonyl, alkylamino, dialkylamino, alkoxycarbonyl, dialkoxy(thio)phosphoryl, alkenyl, alkenyloxy, alkenylamino, alkylideneamino, alkenyloxycarbonyl, alkinyl, alkinyloxy, alkinylamino, alkinyloxycarbonyl, cycloalkyl, cycloalkyloxy, cycloalkylalkyl, cycloalkylalkoxy, cycloalkylideneamino, cycloalkyloxycarbonyl, cycloalkylalkoxycarbonyl, aryl, aryloxy, arylalkyl, arylalkoxy, aryloxycarbonyl, arylalkoxycarbonyl, heterocyclyl, heterocyclylalkyl, heterocyclylalkoxy or heterocyclylalkoxycarbonyl, or the radicals $R^2$ and $R^3$ together represent one of the following groupings

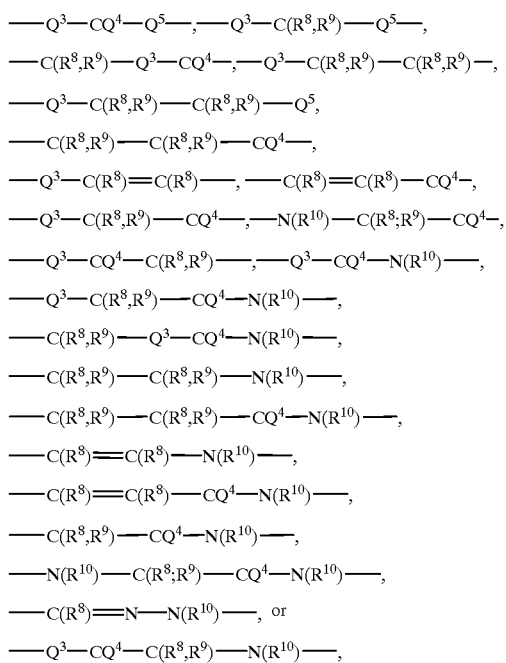

wherein
- $Q^3$, $Q^4$ and $Q^5$ are identical or different and in each case represent oxygen or sulphur,
- $R^8$ and $R^9$ are identical or different and individually represent hydrogen, halogen or alkyl, or together represent alkanediyl and
- $R^{10}$ represents hydrogen or hydroxyl, or represents optionally cyano-, halogen-, alkoxy-, alkylcarbonyl- or alkoxy-carbonyl-substituted alkyl, alkylcarbonyl, alkoxycarbonyl or alkylsulphonyl, or represents in each case optionally halogen-substituted alkenyl or Blkinyl, or represents in each case optionally halogen- or alkyl-substituted cycloalkyl or cycloalkylalkyl, or represents in each case optionally halogen-substituted alkoxy or alkenyloxy, or represents in each case optionally cyano-, halogen-, alkyl-, halogenoalkyl-, alkoxy- or halogenoalkoxy-substituted arylalkyl or arylalkoxy,
- $R^4$ represents amino, alkyl, halogenoalkyl or cycloalkyl,
- $R^5$ represents hydrogen, alkyl or halogenoalkyl,
- $R^6$ represents hydrogen or alkyl and
- $R^7$ represents hydrogen, alkyl, alkylcarbonyl, alkoxycarbonyl, alkylarninocarbonyl, dialkylaminocarbonyl or alkylsulphonyl, or
- $R^6$ and $R^7$ together represent alkanediyl or an alkylideneimino, cycloalkylalkylideneimino or arylalkylideneimino grouping, have now been found.

The new substituted diazacyclohexanedi(thi)ones of the general formula (I) are obtained if uracils of the general formula (II)

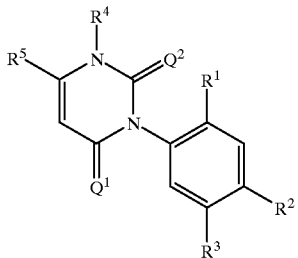

in which
Q$^1$, Q$^2$, R$^1$, R$^2$, R$^3$, R$^4$ and R$^5$ have the abovementioned meanings, are reacted with ammonia, if appropriate in the presence of a diluent, and, if appropriate, the compounds thus obtained of the formula (I) in which R$^6$ and R$^7$ represent hydrogen are reacted with alkylating, acylating or sulphonylating agents by customary methods.

The new substituted diazacyclahexanedi(thi)ones of the general formula (I) are distinguished by a potent and selective herbicidal activity.

In the definitions, the saturated or unsaturated hydrocarbon chains, such as alkyl, alkanediyl, alkenyl or alkinyl—also in combination with heteroatoms, such as in alkoxy, alkylthio or alkylamino—are in each case straight-chain or branched.

Halogen in general represents fluorine, chlorine, bromine or iodine, preferably fluorine, chlorine or bromine, in particular fluorine or chlorine.

The invention preferably relates to compounds of the formula (I) in which

Q$^1$ represents oxygen or sulphur,

Q$^2$ represents oxygen or sulphur,

R$^1$ represents hydrogen, cyano, nitro, fluorine, chlorine or bromine, or represents optionally fluorine- and/or chlorine-substituted alkyl or alkoxy having in each case 1 to 4 carbon atoms, R$^2$ represents hydrogen, cyano, nitro, thiocarbamoyl, fluorine, chlorine or bromine, or represents in each case optionally fluorine- and/or chlorine-substituted alkyl or alkoxy having in each case 1 to 4 carbon atoms, R$^3$ represents the following grouping

—A$^1$—A$^2$—A$^3$ in which
A$^1$ represents a single bond, or represents oxygen, sulphur, —SO—, —SO$_2$—, —CO—or the grouping —N—A$^4$—, wherein A$^4$ represents hydrogen, hydroxyl, C$_1$–C$_4$-alkyl, C$_1$–C$_4$-alkoxy, phenyl, C$_1$–C$_4$-alkylsulphonyl or phenylsulphonyl, A$^1$ furthermore represents in each case optionally fluorine-, chlorine- or bromine-substituted C$_1$–C$_6$-alkanediyl, C$_2$–C$_6$-alkenediyl, C$_2$–C$_6$-azaalkenediyl, C$_2$–C$_6$alkinediyl, C$_3$–C$_6$-cycloalkanediyl, C$_3$–C$_6$-cycloalkenediyl or phenylene, A$^2$ represents a single bond, or represents oxygen, sulphur, —SO—, —SO$_2$—, —CO—or the grouping —N—A$^4$—, wherein A$^4$ represents hydrogen, hydroxyl, C$_1$–C$_4$-alkyl, C$_1$–C$_4$-alkoxy, phenyl, C$_1$–C$_4$-alkylsulphonyl or phenylsulphonyl, A$^2$ furthermore represents in each case optionally fluorine-, chlorine- or bromine-substituted C$_1$–C$_6$-alkanediyl, C$_2$–C$_6$-alkenediyl, C$_2$–C$_6$-azaalkenediyl, C$_2$–C$_6$alkinediyl, C$_3$–C$_6$-cycloalkanediyl, C$_3$–C$_6$-cycloalkenediyl or phenylene, A$^3$ represents hydrogen, hydroxyl, mercapto, amino, cyano, isocyano, thiocyanato, nitro, carboxyl, carbamoyl, thiocarbamoyl, sulpho, chlorosulphonyl or halogen, or represents in each case optionally halogen- or C$_1$–C$_4$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups, or represents in each case optionally halogen-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, or represents in each case optionally halogen-, cyano-, carboxyl-, C$_1$–C$_4$-alkyl- and/or C$_1$–C$_4$-alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and, where appropriate, 1 to 4 carbon atoms in the alkyl groups, or represents in each case optionally nitro-, cyano-, carboxyl-, halogen, C$_1$–C$_4$-alkyl-, C$_1$–C$_4$-halogenoalkyl-, C$_1$–C$_4$-alkyloxy-, C$_1$–C$_4$-halogenoalkyloxy-and/or C$_1$–C$_4$-alkoxy-carbonyl-substituted phenyl, phenyloxy, phenyl-C$_1$–C$_4$-alkyl, phenyl-C$_1$–C$_4$-alkoxy, phenyloxycarbonyl or phenyl-C$_1$–C$_4$-alkoxycarbonyl, oxetanyl, (in each case optionally completely or partly hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-C$_1$–C$_4$-alkyl, furyl-C$_1$–C$_4$-alkyl, thienyl-C$_1$–C$_4$-alkyl, oxazolyl-C$_1$–C$_4$-alkyl, isoxazole-C$_1$–C$_4$-alkyl, thiazole-C$_1$–C$_4$-alkyl, pyridinyl-C$_1$–C$_4$-alkyl, pyrimidinyl-C$_1$–C$_4$-alkyl, pyrazolylmethoxy or furylmethoxy, or represents perhydropyranylmethoxy or pyridylmethoxy, or the radicals R$^2$ and R$^3$ together represent one of the following groupings

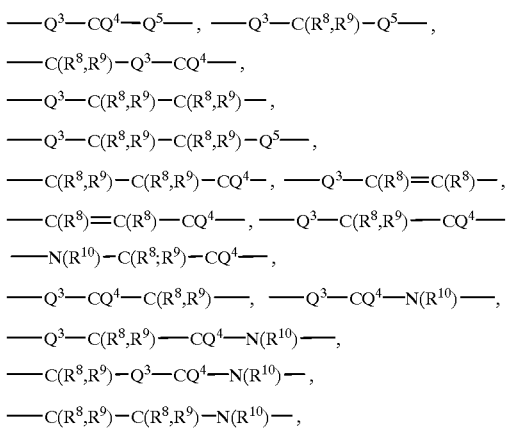

-continued

—C(R$^8$,R$^9$)—C(R$^8$,R$^9$)—CQ$^4$—N(R$^{10}$)—,

—C(R$^8$)═C(R$^8$)—N(R$^{10}$)—,

—C(R$^8$)═C(R$^8$)—CQ$^4$—N(R$^{10}$)—,

—C(R$^8$,R$^9$)—CQ$^4$—N(R$^{10}$)—,

—N(R$^{10}$)—C(R$^8$;R$^9$)—CQ$^4$—N(R$^{10}$)—,

—C(R$^8$)═N—N(R$^{10}$)—, or

—Q$^3$—CQ$^4$—C(R$^8$,R$^9$)—N(R$^{10}$)—, wherein
Q$^3$, Q$^4$ and Q$^5$ are identical or different and in each case represent oxygen or sulphur,
R$^8$ and R$^9$ are identical or different and individually represent hydrogen, fluorine, chlorine, bromine or C$_1$–C$_4$-alkyl, or together represent C$_2$–C$_5$-alkanediyl and
R$^{10}$ represents hydrogen or hydroxyl, or represents optionally cyano-, fluorine-, chlorine-, C$_1$–C$_4$-alkoxy-, C$_1$–C$_4$-alkyl-carbonyl- or C$_1$–C$_4$-alkoxy-carbonyl-substituted alkyl, alkylcarbonyl, alkoxycarbonyl or alkylsulphonyl having in each case 1 to 6 carbon atoms in the alkyl groups, or represents in each case optionally fluorine-, chlorine- or bromine-substituted alkenyl or alkinyl having in each case 2 to 6 carbon atoms, or represents in each case optionally fluorine-, chlorine-, bromine- or C$_1$–C$_4$-alkyl-substituted cycloalkyl or cycloalkylalkyl having in each case 3 to 6 carbon atoms in the cycloalkyl groups and, where appropriate, 1 to 3 atoms in the alkyl group, or represents in each case optionally fluorine- and/or chlorine-substituted alkoxy or alkenyloxy having in each case up to 6 carbon atoms, or represents in each case optionally cyano-, fluorine-, chlorine-, C$_1$–C$_4$-alkyl-, C$_1$–C$_4$-halogenoalkyl-, C$_1$–C$_4$-alkoxy- or C$_1$–C$_4$-halogenoalkoxy-substituted benzyl or benzyloxy, R$^4$ represents amino or represents optionally fluorine- and/or chlorine-substituted alkyl having 1 to 4 carbon atoms, or represents cycloalkyl having 3 to 6 carbon atoms, R$^5$ represents hydrogen, or represents optionally fluorine- and/or chlorine-substituted alkyl having 1 to 4 carbon atoms, R$^6$ represents hydrogen or alkyl having 1 to 4 carbon atoms and R$^7$ represents hydrogen, or represents alkyl, alkylcarbonyl, alkoxycarbonyl, alkylaminocarbonyl, dialkylaminocarbonyl or alkylsulphonyl having in each case 1 to 4 carbon atoms in the alkyl groups, or R$^6$ and R$^7$ together represent alkanediyl having 2 to 6 carbon atoms or an alkylideneimino, cycloalkylalkylideneimino or arylalkylideneimino grouping having in each case up to 6 carbon atoms in the alkylidene part and, where appropriate, 5 or 6 carbon atoms in the cycloalkyl part or 6 or 10 carbon atoms in the aryl part.

The invention particularly relates to compounds of the formula (I) in which

Q$^1$ represents oxygen,
Q$^2$ represents oxygen,
R$^1$ represents hydrogen, fluorine or chlorine,
R$^2$ represents cyano, chlorine, bromine, methyl or trifluoromethyl,
R$^3$ represents the following grouping

—A$^1$—A$^2$—A$^3$ in which
A$^1$ represents a single bond, or represents oxygen, sulphur, —SO—, —SO$_2$—, —CO—or the grouping —N—A$^4$—, wherein A$^4$ represents hydrogen, hydroxyl, methyl, ethyl, n- or i-propyl, methoxy, ethoxy, n- or i-propoxy, methylsulphonyl or ethylsulphonyl, A$^1$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, A$^2$ represents a single bond, or represents oxygen, sulphur, —SO—, —SO$_2$—, —CO—or the grouping —N—A$^4$—, wherein A$^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, A$^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, A$^3$ represents hydrogen, hydroxyl, amino, cyano, nitro, carboxyl, carbamoyl, sulpho, fluorine, chlorine or bromine, or represents in each case optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl or dipropoxyphosphoryl or diisopropoxyphosphoryl, or represents in each case optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, or represents in each case optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl or cyclohexylmethoxycarbonyl, or represents in each case optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl, oxetanyl, (in each case optionally completely or partly hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienyltnethyl, oxazolylmethyl, isoxazolemethyl, thiazolemethyl, pyridinylmethyl, pyrimidinylmethyl, pyrazolylmethoxy, furylmethoxy or pyridylmethoxy, or the radicals $R^2$ and $R^3$ together represent one of the following groupings

—$Q^3$—$CQ^4$—$Q^5$—, —$Q^3$—$C(R^8,R^9)$—$Q^5$—,

—$C(R^8,R^9)$—$Q^3$—$CQ^4$—,

—$Q^3$—$C(R^8,R^9)$—$C(R^8,R^9)$—,

—$Q^3$—$C(R^8,R^9)$—$C(R^8,R^9)$—$Q^5$—,

—$C(R^8,R^9)$—$C(R^8,R^9)$—$CQ^4$—, —$Q^3$—$C(R^8)$=$C(R^8)$—,

—$C(R^8)$=$C(R^8)$—$CQ^4$—, —$Q^3$—$C(R^8,R^9)$—$CQ^4$—

—$N(R^{10})$—$C(R^8;R^9)$—$CQ^4$—,

—$Q^3$—$CQ^4$—$C(R^8,R^9)$—, —$Q^3$—$CQ^4$—$N(R^{10})$—,

—$Q^3$—$C(R^8,R^9)$—$CQ^4$—$N(R^{10})$—,

—$C(R^8,R^9)$—$Q^3$—$CQ^4$—$N(R^{10})$—,

—$C(R^8,R^9)$—$C(R^8,R^9)$—$N(R^{10})$—,

—$C(R^8,R^9)$—$C(R^8,R^9)$—$CQ^4$—$N(R^{10})$—,

—$C(R^8)$=$C(R^8)$—$N(R^{10})$—,

—$C(R^8)$=$C(R^8)$—$CQ^4$—$N(R^{10})$—,

—$C(R^8,R^9)$—$CQ^4$—$N(R^{10})$—,

—$N(R^{10})$—$C(R^8;R^9)$—$CQ^4$—$N(R^{10})$—,

—$C(R^8)$=$N$—$N(R^{10})$—, or

—$Q^3$—$CQ^4$—$C(R^8,R^9)$—$N(R^{10})$—, wherein $Q^3$, $Q^4$ and $Q^5$ are identical or different and in each case represent oxygen or sulphur, $R^8$ and $R^9$ are identical or different and individually represent hydrogen, fluorine, chlorine, methyl or ethyl, or together represent ethane-1,2-diyl (dimethylene), and $R^{10}$ represents hydrogen or hydroxyl, or represents optionally cyano-, fluorine-, chlorine-, methoxy-, ethoxy-, acetyl-, propionyl-, methoxycarbonyl- or ethoxycarbonyl-substituted methyl, ethyl, n- or i-propyl or n-, i-, s- or t-butyl, or represents in each case optionally fluorine-, chlorine- or bromine-substituted propenyl, butenyl, propinyl or butinyl, or represents in each case optionally fluorine-, chlorine-, bromine-, methyl- or ethyl-substituted cyclopropyl, cyclobutyl, cyclopentyl, cyclohexyl, cyclopropylmethyl, cyclobutylinethyl, cyclopentylmethyl or cyclohexylmethyl, or represents in each case optionally fluorine- and/or chlorine-substituted methoxy, ethoxy, n- or i-propoxy, n-, i- or s-butoxy, propenyloxy or butenyloxy, or represents in each case optionally cyano-, fluorine-, chlorine-, methyl-, ethyl-, trifluoromethyl-, methoxy-, ethoxy-, difluoromethoxy- or trifluoromethoxy-substituted benzyl or benzyloxy, $R^4$ represents amino, methyl, ethyl, n- or i-propyl or cyclopropyl, $R^5$ represents in each case optionally fluorine- and/or chlorine-substituted methyl or ethyl, $R^6$ represents hydrogen, methyl or ethyl and $R^7$ represents hydrogen, methyl, ethyl, acetyl, propionyl, methoxycarbonyl, ethoxycarbonyl, methylaminocarbonyl, ethylaminocarbonyl, dimethylaminocarbonyl, methylsulphonyl or ethylsulphonyl.

The definitions of radicals listed above, general or mentioned in preferred ranges, apply both to the end products of the formula (I) and accordingly to the particular starting substances or intermediate products required for the preparation. These definitions of radicals can be combined with one another as desired, that is to say also between the stated ranges of preferred compounds.

Examples of the compounds of the formula (I) according to the invention are listed in the following groups.

GROUP 1

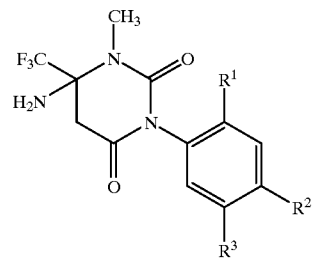

(IA-1)

In this formula, $R^1$, $R^2$ and $R^3$ have the meanings given in the following list

| Example No. | $R^1$ | $R^2$ | $R^3$ |
|---|---|---|---|
| 1 | F | F | F |
| 2 | F | Cl | F |
| 3 | F | Cl | Cl |
| 4 | Cl | F | F |
| 5 | F | CN | F |
| 6 | F | CN | Cl |
| 7 | F | CN | Br |
| 8 | F | Br | F |
| 9 | F | CN | Cl |
| 10 | F | CH$_3$ | F |

-continued

| Example No. | R¹ | R² | R³ |
|---|---|---|---|
| 11 | F | CF3 | F |
| 12 | F | Cl | CH₃ |
| 13 | F | Cl | —N(CH₃)SO₂C₂H₅ |
| 14 | F | CN | —N(CH₃)SO₂C₂H₅ |
| 15 | Cl | Cl | —N(CH₃)SO₂C₂H₅ |
| 16 | F | CN | —NH—COOCH₃ |
| 17 | F | Cl | OH |
| 18 | Cl | CN | OH |
| 19 | F | Cl | CH(CH₃)2 |
| 20 | F | CN | —NH—SO₂—CH₃ |
| 21 | F | Cl | —SO₂—CH₃ |
| 22 | F | CN | —SO₂—O—CH₃ |
| 23 | F | Cl | —SO₂—NH—CH₃ |
| 24 | F | F | —COOCH₃ |
| 25 | F | CN | —CO—NH—CH₃ |
| 26 | Cl | Cl | —COOCH₃ |
| 27 | Cl | CN | —COOC₂H₅ |
| 28 | F | Cl | —OC₂H₅ |
| 29 | F | CN | —N(C₂H₅)SO₂C₂H₅ |
| 30 | F | CN | —N(SO₂CH₃)₂ |
| 31 | F | Cl | —CO—N(CH₃)₂ |
| 32 | F | Cl | —S—CH₂—C≡CH |
| 33 | Cl | Cl | —S—CH₂—C≡CH |
| 34 | F | CN | —S—CH₂—C≡CH |
| 35 | F | CN | —O—CH(CH₃)—C≡CH |
| 36 | F | Cl | —S—CH₂—COOCH₃ |
| 37 | F | CN | —O—CH₂CH₂—OCH₃ |
| 38 | F | Cl | —O(CH₂CH₂O)₂CH₃ |
| 39 | F | CN | —O—CH₂—CH=CH₂ |
| 40 | F | CN | —O—CH₂—C≡CH |
| 41 | F | Cl | SH |
| 42 | F | Cl | —SCH₃ |
| 43 | F | CN | —SC₂H₅ |
| 44 | F | F | —S—CH(CH₃)₂ |
| 45 | F | CN | —O—CH₂—CF₃ |
| 46 | F | Cl | —O—CH(CH₂F)₂ |
| 47 | F | Cl | —OCHCOOC₂H₅<br>       \|<br>       CH₃ |
| 48 | F | CN | —OCHCOOCH₂C≡CH<br>       \|<br>       CH₃ |
| 49 | F | CN | —NH—SO₂C₂H₅ |
| 50 | Cl | Cl | —NH—SO₂C₂H₅ |
| 51 | Cl | CN | —NH—SO₂C₂H₅ |
| 52 | F | CN | —NH—SO₂CH(CH₃)₂ |
| 53 | F | CN | —NH—SO₂C₄H₉ |
| 54 | F | Cl | —SO₂—NH—C₂H₅ |
| 55 | F | CN | —SO₂—N(CH₃)₂ |
| 56 | F | Cl | —SO₂—NH—CH(CH₃)₂ |
| 57 | F | Cl | —SCN |
| 58 | F | Cl | —SO₂Cl |
| 59 | F | CN | —SO₂Cl |
| 60 | F | Cl | —O—CS—N(CH₃)₂ |
| 61 | F | CN | —S—CO—N(CH₃)₂ |
| 62 | F | Cl | —NH—P(O)(OCH₃)₂ |
| 63 | F | CN | —NH—P(O)(OC₂H₅)₂ |
| 64 | F | CN | —COOCH(CH₃)₂ |
| 65 | F | Cl | —CO—NH—C₂H₅ |
| 66 | F | Cl | —NH—COCH(CH₃)₂ |
| 67 | F | CN | —NH—CO—C(CH₃)₃ |
| 68 | F | Cl | —NH—CO—NH₂ |
| 69 | F | Cl | —NH—CO—NHCH₃ |
| 70 | F | CN | —NH—CO—N(CH₃)₂ |
| 71 | F | CN | —N(COCH₃)₂ |
| 72 | F | Cl | —NH—COCH(CH₃)Cl |
| 73 | F | CN | —S—CH₂—CH=CH₂ |
| 74 | Cl | Cl | —S—CH₂—CH=CH₂ |
| 75 | F | Cl | —S—CH(CH₃)C≡CH |
| 76 | F | CN | —S—CH(CH₃)COOC₂H₅ |
| 77 | F | Cl | —S(O)—CH₃ |

-continued

| Example No. | R¹ | R² | R³ |
|---|---|---|---|
| 78 | F | CN | —S—C(cyclopropyl)—COOCH₃ |
| 79 | F | CN | —S—CH₂—C₆H₅ |
| 80 | F | Cl | —S—C(cyclobutyl)—COOCH₃ |
| 81 | F | CN | —O—(tetrahydrofuran-3-yl) |
| 82 | F | CN | —O—CH₂—(tetrahydrofuran-2-yl) |
| 83 | F | Cl | —O—CH₂—(tetrahydrofuran-2-yl) |
| 84 | F | CN | O—CH₂—CN |
| 85 | F | CN | —O—SO₂CH₃ |
| 86 | F | CN | —OCH₂—CH(Cl)=CH₂ |
| 87 | F | CN | —O—CH₂—COOCH₃ |
| 88 | F | CN | —O—CHF₂ |
| 89 | F | Cl | —OCOOCH₂CH₂Cl |
| 90 | F | Cl | —OCH₂P(O)(OC₂H₅)₂ |
| 91 | Cl | CN | —OCH(CH₃)P(O)(OC₂H₅)₂ |
| 92 | F | Cl | —OCH₂P(O)(OCH₃)₂ |
| 93 | F | CN | —O—N=C(CH₃)₂ |
| 94 | F | CN | —O—N(C₂H₅)₂ |
| 95 | F | CN | —NH—OCH(CH₃)₂ |
| 96 | F | CN | —NH—SO₂—cyclopropyl |
| 97 | F | Cl | —NH—SO₂—cyclopropyl |
| 98 | Cl | Cl | —NH—SO₂—cyclopropyl |
| 99 | F | CN | —NH—SO₂—cyclopentyl |
| 100 | F | Cl | —NH—SO₂—cyclohexyl |
| 101 | F | CN | —NH—SO₂—phenyl |

-continued

| Example No. | R¹ | R² | R³ |
|---|---|---|---|
| 102 | F | Cl | —NH—SO$_2$—CH$_2$—C$_6$H$_5$ |
| 103 | F | CN | —N(C$_2$H$_5$)SO$_2$C$_2$H$_5$ |
| 104 | F | CN | —N(CH$_3$)SO$_2$CH(CH$_3$)$_2$ |
| 105 | Cl | Cl | —N(CH$_3$)SO$_2$C$_2$H$_5$ |
| 106 | Cl | Cl | —N(CH$_3$)SO$_2$C$_4$H$_9$ |
| 107 | H | CN | —N(CH$_3$)SO$_2$C$_2$H$_5$ |
| 108 | F | CN | —N(CH$_3$)SO$_2$CH$_3$ |
| 109 | F | CN | —N(SO$_2$C$_2$H$_5$)$_2$ |
| 110 | F | CN | —N(SO$_2$CH$_3$)SO$_2$C$_2$H$_5$ |
| 111 | F | CN | —N(cyclopropyl)—SO$_2$C$_2$H$_5$ |
| 112 | F | CN | N(CH$_3$)$_2$ |
| 113 | F | Cl | NH$_2$ |
| 114 | Cl | Cl | NH$_2$ |
| 115 | Cl | Cl | —OCH(CH$_3$)$_2$ |
| 116 | F | CN | —OCH(CH$_3$)$_2$ |
| 117 | F | CN | —O—cyclopropyl |
| 118 | Cl | Cl | —O—cyclopropyl |
| 119 | F | CN | —O—CH$_2$—COOC$_2$H$_5$ |
| 120 | F | CN | —S—CH$_2$—COOCH$_3$ |
| 121 | F | CN | —S—CH$_2$—COOC$_2$H$_5$ |
| 122 | Cl | Cl | —S—CH$_2$—COOC$_2$H$_5$ |
| 123 | F | CN | —CH$_2$—CH(Cl)COOCH$_3$ |
| 124 | F | CN | —CH$_2$—CH(Cl)COOC$_2$H$_5$ |
| 125 | F | CN | —CH$_2$—CH(Cl)CONHC$_2$H$_5$ |
| 126 | Cl | Cl | —CH$_2$—CH(Cl)CONHC$_2$H$_5$ |
| 127 | Cl | Cl | —CH$_2$CH(Cl)CONHCH(CH$_3$)$_2$ |
| 128 | F | CN | —CH$_2$CH(Cl)CONHCH(CH$_3$)$_2$ |
| 129 | F | —O—CO—N(CH$_3$)— | |
| 130 | F | —S—CO—N(CH$_3$)— | |
| 131 | H | —O—CH$_2$—CO—N(CH$_3$)— | |
| 132 | F | —O—CH$_2$—CO—N(CH$_3$)— | |
| 133 | H | —O—CH$_2$—O— | |
| 134 | F | —O—CH$_2$—O— | |
| 135 | H | —O—CF$_2$—O— | |
| 136 | F | —O—CF$_2$—O— | |
| 137 | H | —O—CH$_2$CH$_2$—O— | |
| 138 | F | —O—CH$_2$CH$_2$—O— | |
| 139 | H | —O—CF$_2$CF$_2$—O— | |
| 140 | F | —O—CF$_2$CF$_2$—O— | |
| 141 | H | —O—C(CH$_3$)$_2$—O— | |
| 142 | F | —O—C(CH$_3$)$_2$—O— | |
| 143 | F | —O—CH$_2$—CO—N(OCH$_3$)— | |
| 144 | F | —O—CH$_2$—CO—N(CH$_2$—CH=CH$_2$)— | |

-continued
| Example No. | R¹ | R² | R³ |
|---|---|---|---|
| 145 | F | | 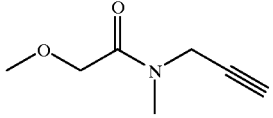 |
| 146 | F | Cl | 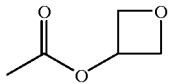 |
| 147 | F | CN | 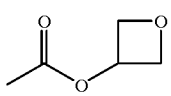 |
| 148 | F | Cl | COOH |
| 149 | F | CN | COOH |
| 150 | F | Cl | —COOCH(CH₃)₂ |
| 151 | F | CN | —COOCH(CH₃)₂ |
| 152 | H | Cl | —COOCH(CH₃)₂ |
| 153 | F | Cl | 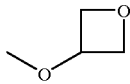 |
| 154 | F | CN | 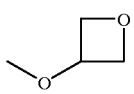 |
| 155 | H | Cl | 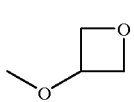 |
In this formula, R¹, R² and R³ have, for example, the meanings given above in Group 1.
In this formula, R¹, R² and R³ have, for example, the meanings given above in Group 1.
GROUP 3
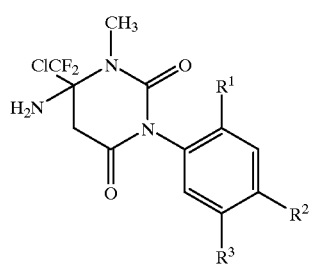
(IA-3)
GROUP 4
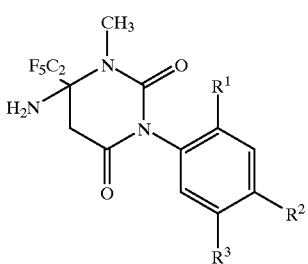
(IA-4)

In this formula, $R^1$, $R_2$ and $R^3$ have, for example, the meanings given above in Group 1.

GROUP 5

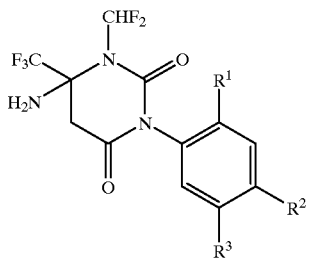
(IA-5)

In this formula, $R^1$, $R^2$ and $R^3$ have, for example, the meanings given above in Group 1.

GROUP 6

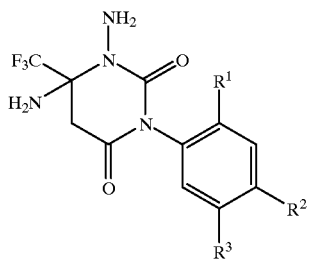
(IA-6)

In this formula, $R^1$, $R^2$ and $R^3$ have, for example, the meanings given above in Group 1.

If, for example, 1-(2,4-dichloro-5-methoxy-phenyl)-3,6-dihydro-2,6-dioxo-3-methyl-4-trifluoromethyl-1(2H)-pyrimidine and ammonia are used as starting substances, the course of the reaction in the process according to the invention can be outlined by the following equation:

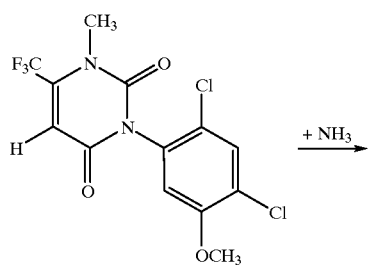

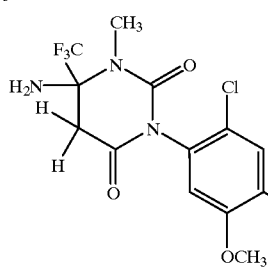

Formula (II) provides a general definition of the uracils to be used as starting substances in the process according to the invention for the preparation of the compounds of the general formula (I). In the formula (II), $R^1$, $R^2$, $R^3$, $R^4$ and $R^5$ preferably or in particular have those meanings which have already been mentioned above as preferred or as particularly preferred for $R^1$, $R^2$, $R^3$, $R^4$ and $R^5$ in connection with the description of the compounds of the formula (I).

The starting substances of the formula (II) are known and/or can be prepared by known processes (cf. U.S. Pat. No. 5,084,084, U.S. Pat. No. 5,127,935, U.S. Pat. No. 5,154,755, U.S. Pat. No. 5,169,430, DE-A 4327743 of 18.8.1993, Preparation Examples).

The starting substances of the formula (II) can be prepared in accordance with the following equation:

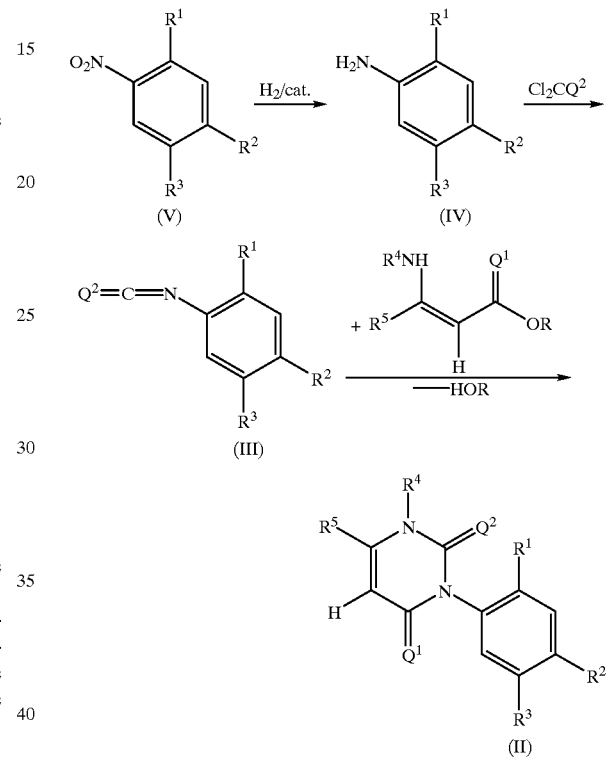

Of the compounds of the formulae (II), (III) and (IV), in each case the one in which $R^1$ represents fluorine or chlorine, $R^2$ represents cyano or methyl and $R^3$ represents amino or nitro are not yet known from the literature, and, as new substances, the present application relates to them.

Instead of the compounds of the formula (III), compounds of the formula (VI)

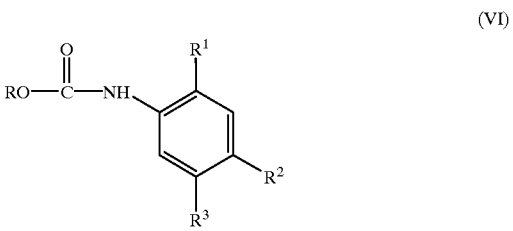
(VI)

wherein $R^1$, $R^2$ and $R^3$ are defined as above and R represents alkyl (in particular methyl or ethyl), aryl (in particular phenyl) or aralkyl (in particular benzyl), can also be employed here with the same result.

Possible diluents for carrying out the process according to the invention are the customary organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; esters, such as methyl acetate or ethyl acetate, sulphoxides, such as dimethyl sulphoxide, alcohols, such as methanol, ethanol or n- or i-propanol, ethylene glycol monomethyl ether, ethylene glycol monoethyl ether, diethylene glycol monomethyl ether or diethylene glycol monoethyl ether, mixtures thereof with water or pure water.

The reaction temperatures can be varied within a substantial range in carrying out the process according to the invention. The reaction is in general carried out at temperatures between –100° C. and +40° C., preferably at temperatures between –80° C. and +20° C., in particular at temperatures between –60° C. and 0° C. The process according to the invention is in general carried out under normal pressure. However, it is also possible to carry out the process under increased or reduced pressure—in general between 0.1 bar and 10 bar.

For carrying out the process according to the invention, the particular starting substances required are in general employed in approximately equimolar amounts. However, it is also possible to use one of the two particular components employed in a relatively large excess. The reactions are in general carried out in a suitable diluent, and the reaction mixture is stirred at the particular temperature required for several hours. Working up is in each case carried out by customary methods in the process according to the invention (cf. the Preparation Examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonurn, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotvledon crops of the genera: Oryza, Zea, Triticum, Hordeum, Avena, Secale, Sorghum, Panicum, Saccharun, Ananas, Asparagus and Allium. -

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are particularly suitable for selectively controlling monocotyledon and dicotyledon weeds in monocotyledon and dicotyledon crops both by the pre-emergence and by the post-emergence method.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations if polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl. sulphoxide, and water.

Suitable solid carriers are:

for example anunonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Farther additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, such as, for example, anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop(-methyl), fenoxaprop(-ethyl), fluazifop(-butyl), haloxyfop(-methyl) and quizalofop(-ethyl); azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, chlornethoxynil (X-52), chlomitrofen, fluoroglycofen, fomesafen, halosafen, lactofen, nitrofen and oxyfluorfen; ureas such as, for example, chlortoluron, cumyluron (JC-940), diuron, dymnron (daimuron), fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, AC-014 (AC-322140), amidosulfuron, bensulfuron(-methyl), chlorimuron(-ethyl), chlorsulfuron, cinosulfuron, DPX-47, HOE-404, imazosulfuron, metsulfuron(-methyl), nicosulfuron, primisulfuron, pyrazosulfuron(-ethyl), thifensulfuron(-methyl), triasulfuron and tribenuron(-methyl); thiocarbamates such as, for example, butylate, cycloate, diallate, dimepiperate, EPTC, esprocarb, molinate, prosulfocarb, thiobencarb (benthiocarb) and triallate; triazines such as, for example, atrazine, cyanazine, dimethametryn, prometryne, simazine, simetryne, terbutryne and terbutylazine; triazinones such as, for example, hexazinone, metamitron and metribuzin; others such as, for example, aminotriazole, benfuresate, bensulide, bentazone, benzofenap, bromobutide, butamifos, cafenstrole (CH-900), cinmethylin, clomazone, clomeprop, clopyralid, DEH-112, difenzoquat, dimethenamid, dithiopyr, ethofumesate, flumetsulam, fluorochloridone, glufosinate, glyphosate, amiprophos(-methyl), anilofos, etobenzanid (HW-52), isoxaben, KPP-314, KUH-833, KUH-911, KUH-920, MK-243, naproanilide, NSK-850, oxadiazon, piperophos, propanil, pyrazolate, pyrazoxyfen, pyributicarb, pyridate, quinchlorac, quinmerac, sulphosate and tridiphane.

Mixing with other known active compounds such as fungicides, insecticides, acaricides, nematicides, bird repellants, plant nutrients and soil conditioners, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the examples which follow.

PREPARATION EXAMPLES

Example 1

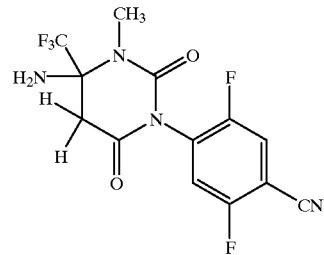

Ammonia (gas) is passed into a mixture of 0.80 g (2.4 mmol) of 1-(4-cyano-2,5-difluoro-phenyl)-3,6-dihydro-2,6-dioxo-3-methyl-4-trifluoromethyl-1(2H)-pyrimidine and 20 ml of tetrahydrofuran at −60° C. for 10 minutes, while stirring. The mixture is allowed to come to room temperature (about 20° C.) overnight (about 15 hours), while stirring, and is then diluted to about twice the volume with diethyl ether, and the solution is washed with 5% strength aqueous sodium dihydrogenphosphate solution, dried over sodium sulphate and filtered. The solvent is then distilled off carefully from the filtrate under a water-pump vacuum.

0.70 g (93% of theory) of 1-(4-cyano-2,5-difluoro-phenyl)-4-amino-2,6-dioxo-3-methyl-4-trifluoromethyl-1,3-diaza-cyclohexane is obtained as a crystalline residue of melting point 115° C.

The compounds of the formula (I) listed in the following Table 1, for example, can also be prepared analogously to Example 1 and in accordance with the general description of the preparation process according to the invention.

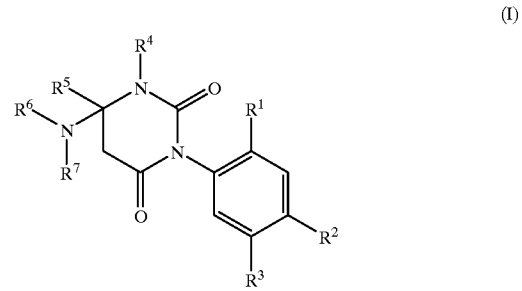

TABLE 1

Examples of the compounds of the formula (I)

| Example No. | $R^1$ | $R^2$ | $R^3$ | $R^4$ | $R^5$ | $R^6$ | $R^7$ | Physical data |
|---|---|---|---|---|---|---|---|---|
| 2 | F | CN | $N(CH_3)SO_2C_2H_5$ | $CH_3$ | $CF_3$ | H | H | 1H NMR (DMSO-D6, δ) 8.17 ppm |
| 3 | F | CN | $NHSO_2C_2H_5$ | $CH_3$ | $CF_3$ | H | H | m.p.: 82° C. |
| 4 | F | CN | $N(CH_3)SO_2CH_3$ | $CH_3$ | $CF_3$ | H | H | m.p.: 108° C. |
| 5 | F | CN | $NHSO_2CH_3$ | $CH_3$ | $CF_3$ | H | H | m.p.: 221° C. |
| 6 | F | CN | $OCH_3$ | $CH_3$ | $CF_3$ | H | H | |
| 7 | F | CN | $SCH_3$ | $CH_3$ | $CF_3$ | H | H | |
| 8 | F | CN | $SO_2CH_3$ | $CH_3$ | $CF_3$ | H | H | |
| 9 | F | Cl | $SO_2NHCH_3$ | $CH_3$ | $CH_3$ | H | H | |
| 10 | H | Cl | $O-CH_2C\equiv CH$ | $CHF_2$ | $CF_3$ | H | H | |
| 11 | F | CN | $O-CHC\equiv CH$ \| $CH_3$ | $CH_3$ | $CF_3$ | H | H | |
| 12 | F | Cl | $NHCO_2CH_3$ | $NH_2$ | $CF_3$ | H | $CO_2CH_3$ |  |
| 13 | F | Cl | CHO | $CH_3$ | $CF_3$ | H | H | |
| 14 | F | CN | $CO_2CH_3$ | $CH_2CH_3$ | $CF_3$ | H | $COCH_3$ | |
| 15 | H | Cl | $CH=CH-CO_2C_2H_5$ | 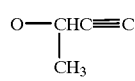 | $CF_3$ | H | $SO_2CH_3$ | |
| 16 | H | Cl |  | $CH_3$ | $CF_3$ | H | H | |
| 17 | F | Cl | $O-CH_2CO_2CH_3$ | $CH_3$ | $CF_3$ | \multicolumn{2}{c}{$-(CH_2)_4-$} | |
| 18 | F | Br | 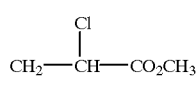 | $CH_3$ | H | $CH_3$ | $CH_3$ | |
| 19 | F | Cl | $-NH-CH_2-COOC_2H_5$ | $CH_3$ | $CF_3$ | H | $CH_3$ | |
| 20 | F | Cl | 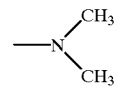 | $CH_3$ | $CF_3$ | H | H | |
| 21 | F | Cl | 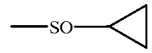 | $CH_3$ | $C_2F_5$ | H | H | |
| 22 | F | Cl | 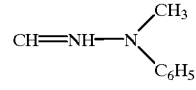 | $CH_3$ | $CF_3$ | H | $CH_3$ | |
| 23 | F | Cl | 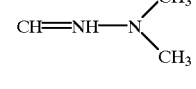 | $CH_3$ | $CF_3$ | H | H | |
| 24 | F | Cl | OH | $CH_3$ | $CF_3$ | H | H | |
| 25 | F | Cl | SH | $CH_3$ | $CF_3$ | H | H | |
| 26 | H | Cl | OH | $CH_3$ | $CF_3$ | H | H | |
| 27 | H | Cl | SH | $CH_3$ | $CF_3$ | H | H | |
| 28 | H | Cl | $NH_2$ | $CH_3$ | $CF_3$ | H | H | |
| 29 | H | CN | $NH_2$ | $CH_3$ | $CF_3$ | H | H | |
| 30 | F | Cl | $CH_2-Br$ | $CH_3$ | $CF_3$ | H | H | |
| 31 | H | Cl | $CH_2-Br$ | $CH_3$ | $C_2F_5$ | H | H | |
| 32 | H | CN | $COOC_2H_5$ | $C_2H_5$ | $CF_3$ | H | H | |
| 33 | F | Cl | Br | $CH_3$ | $CF_3$ | $CH_3$ | $CH_3$ | |
| 34 | F | $NO_2$ | $OCH_3$ | $CH_3$ | $CF_3$ | H | H | |
| 35 | F | $NH_2$ | $OCH_3$ | $CH_3$ | $CF_3$ | H | H | |

TABLE 1-continued

Examples of the compounds of the formula (I)

| Example No. | R¹ | R² | R³ | R⁴ | R⁵ | R⁶ | R⁷ | Physical data |
|---|---|---|---|---|---|---|---|---|
| 36 | F | OH | SCH$_2$COOC$_2$H$_5$ | C$_2$H$_5$ | CH$_3$ | H | H | |
| 37 | F | OCH$_3$ | NHSO$_2$CH$_3$ | CH$_3$ | CF$_3$ | H | H | |
| 38 | H | CSNH$_2$ | NHSO$_2$CH$_3$ | CH$_3$ | CF$_3$ | H | H | |
| 39 | F | CSNH$_2$ | NHSO$_2$CH$_3$ | CH$_3$ | CF$_3$ | H | H | |
| 40 | F | CSNH$_2$ | NHSO$_2$C$_2$H$_5$ | CH$_3$ | CF$_3$ | H | H | |
| 41 | F | CSNH$_2$ | NHSO$_2$C$_3$H$_7$ | CH$_3$ | CF$_3$ | H | H | |
| 42 | F | CSNH$_2$ | NHSO$_2$i-C$_3$H$_7$ | CH$_3$ | CF$_3$ | H | H | |
| 43 | F | CSNH$_2$ | NHSO$_2$C$_4$H$_9$ | CH$_3$ | CF$_3$ | H | H | |
| 44 | F | CSNH$_2$ | N(SO$_2$CH$_3$)(CH$_3$) | CH$_3$ | CF$_3$ | H | H | |
| 45 | F | F | O—CH$_2$—CH=CH$_2$ | C$_2$H$_5$ | CF$_3$ | H | H | |
| 46 | F | CF$_3$ | OCH$_3$ | CH$_3$ | CH$_3$ | CH$_3$ | CH$_3$ | |
| 47 | F | CN | NHSO$_2$CH$_3$ | CHF$_2$ | CH$_3$ | H | H | |
| 48 | F | CN | NHSO$_2$C$_2$H$_5$ | CHF$_2$ | CF$_3$ | H | H | |
| 49 | H | Cl | —P(O)(OCH$_3$)$_2$ | CH$_3$ | CH$_3$ | H | H | |
| 50 | Cl | Cl | NHSO$_2$CH$_3$ | CH$_3$ | CF$_3$ | H | H | |
| 51 | Cl | CN | NHSO$_2$C$_3$H$_7$ | CH$_3$ | CF$_3$ | H | H | |
| 52 | CN | CN | NHSO$_2$C$_2$H$_5$ | CH$_3$ | CF$_3$ | H | CH$_3$ | |
| 52 | F | Cl | OCH$_3$ | CH$_3$ | CF$_3$ | | H$_3$C—C(=O)—CH$_3$ | |
| 53 | F | Cl | H | CH$_3$ | CF$_3$ | H | H | m.p.: 107° C. |
| 54 | F | Cl | SO$_2$NH$_2$ | CH$_3$ | CF$_3$ | H | H | m.p.: 75° C. |
| 55 | F | CN | NHSO$_2$C$_3$H$_7$-n | CH$_3$ | CF$_3$ | H | H | m.p.: 53° C. |
| 56 | F | CN | NHSO$_2$CH(CH$_3$)$_2$ | CH$_3$ | CF$_3$ | H | H | m.p.: 219° C. |
| 57 | F | CN | H | CH$_3$ | CF$_3$ | H | H | m.p.: 160° C. |
| 58 | F | Cl | N(SO$_2$C$_2$H$_5$)$_2$ | CH$_3$ | CF$_3$ | H | H | m.p.: 57° C. |
| 59 | F | F | NO$_2$ | CH$_3$ | CF$_3$ | H | H | |
| 60 | F | CN | NO$_2$ | CH$_3$ | CF$_3$ | H | H | |
| 61 | CN | F | NO$_2$ | CH$_3$ | CF$_3$ | H | H | |
| 62 | F | Cl | NO$_2$ | CH$_3$ | CF$_3$ | H | H | |
| 63 | Cl | Cl | NO$_2$ | CH$_3$ | CF$_3$ | H | H | |
| 64 | F | Cl | NH$_2$ | CH$_3$ | CF$_3$ | H | H | |
| 65 | F | CN | NH$_2$ | CH$_3$ | CF$_3$ | H | H | |
| 66 | F | Cl | —NH—SO$_2$—C$_2$H$_5$ | CH$_3$ | CF$_3$ | H | H | |
| 67 | F | Cl | —NH—SO$_2$—CH(CH$_3$)$_2$ | CH$_3$ | CF$_3$ | H | H | |
| 68 | F | Cl | —NH—SO$_2$—CH$_3$ | CH$_3$ | CF$_3$ | H | H | |
| 69 | F | Cl | NH—SO$_2$—C$_3$H$_7$-n | CH$_3$ | CF$_3$ | H | H | |

STARTING SUBSTANCES OF THE FORMULA (II)

Example (II-1)

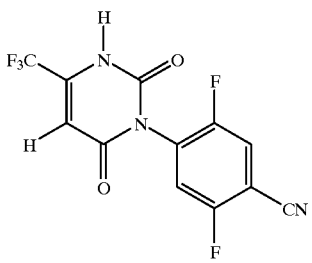

1.8 g (10 mmol) of ethyl 3-amino-4,4,4-trifluoro-crotonate are initially introduced into 30 ml of dimethylformamide and 2 ml of toluene, and 0.3 g (10 mmol) of sodium hydride (80% strength) is added at 0° C. to 5° C. The mixture is stirred at 0° C. to 5° C. for 30 minutes. After the mixture has been cooled to −70° C., 0.9 g (5 mmol) of 4-cyano-2,5-difluoro-phenyl isocyanate—dissolved in 10 ml of toluene—is added and the mixture is stirred at −60° C. to −70° C. for 150 minutes. After removal of the cooling bath, 2 ml of acetic acid are added. The mixture is then diluted with water to about twice the volume and extracted with ethyl acetate. The organic phase is concentrated and the residue is crystallized with diisopropyl ether.

1.1 g (69% of theory) of 1-(4-cyano-2,5-difluoro-phenyl)-3,6-dihydro-2,6-dioxo-4-trifluoromethyl-1(2H)-pyrimidine of melting point 194° C. are obtained.

Example (II-2)

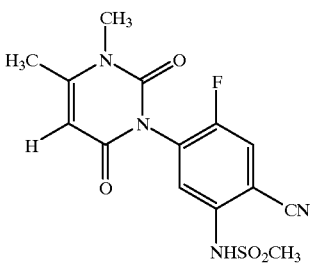

A mixture of 0.83 g (3 mmol) of 1-(4-cyano-2,5-difluoro-phenyl)-3,6-dihydro-2,6-dioxo-3,4-dimethyl-1(2H)-pyrimidine, 0.32 g (3 mmol) of methanesulphonamide, 0.6 g of potassium carbonate and 10 ml of dimethylsulphoxide is heated at 120° C. for 10 hours. After cooling, the mixture is poured onto ice-water and acidified with 2N hydrochloric acid. It is then extracted with ethyl acetate and the organic phase is washed with water, dried with sodium sulphate and filtered. The solvent is distilled off carefully from the filtrate under a water-pump vacuum.

0.8 g (76% of theory) of 1-(4-cyano-2-fluoro-5-methylsulphonylamino)-3,6-dihydro-2,6-dioxo-3,4-dimethyl-1(2H)-pyrimidine is obtained as a crystalline residue (melting point >250° C.).

USE EXAMPLES

Example A

Post-Emergence Test

Solvent: 5 parts by weight of acetone
Emulsifier: 1 part by weight of alkylaryl polyglycol ether To produce a suitable preparation of the active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen such that the particular amounts of active compound desired are applied in 2,000 l of water/ha. After three weeks, the degree of damage to the plants is rated in % damage in comparison to the development of the untreated control.

The figures denote:
0%=no action (like untreated control)
100%=total destruction In this test, for example, Preparation Example (1) shows, when applied in an amount of only 60 g/ha and with a very good tolerance with respect to crop plants, such as, for example, barley (10%), a very potent action against weeds such as Panicum (90%), Abutilon (100%), Amaranthus (100%), Ambrosia (100%), Chenopodium (100%), Datura (100%) and Solanum (100%).

Example B

Pre-Emergence Test

Solvent: 5 parts by weight of acetone
Emulsifier: 1 part by weight of alkylaryl polyglycol ether To produce a suitable preparation of the active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, Preparation Example (1) shows, when applied in an amount of only 30 g/ha and with a very good tolerance with respect to crop plants, such as, for example, maize (0%), a very potent action against weeds such as Digitaria (95%), Abutilon (100%), Chenopodium (100%), Datura (100%), Galinsoga (100%), Matricaria (100%) and Solanum (100%).

We claim:

1. A diazacyclohexanedi(thi)one of the formula (I)

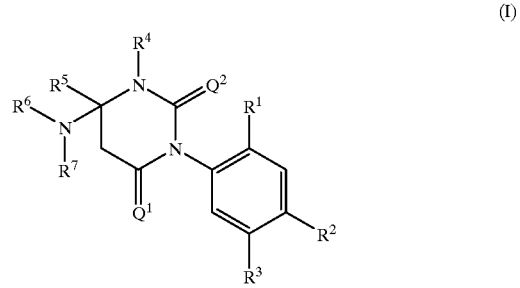

wherein
$Q^1$ represents oxygen,
$Q^2$ represents oxygen,
$R^1$ represents hydrogen, fluorine or chlorine,
$R^2$ represents cyano, chlorine, bromine, methyl or trifluoromethyl,
$R^3$ represents the following grouping

in which
$A^1$ represents a single bond, or represents oxygen, sulphur, —SO—, —SO$_2$—, —CO— or the grouping —N—A$^4$—, wherein A$^4$ represents hydrogen, hydroxyl, methyl, ethyl, n- or i-propyl, methoxy, ethoxy, n- or i-propoxy, methylsulphonyl or ethylsulphonyl, or represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^2$ represents a single bond, or represents oxygen, sulphur, —SO—, —SO$_2$—, —CO—or the grouping —N—A$^4$—, wherein A$^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, or represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^3$ represents hydrogen, hydroxyl, amino, cyano, nitro, carboxyl, carbamoyl, sulpho, fluorine, chlorine or bromine, or represents in each case optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t- pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethyoxyphosphoryl or dipropoxyphosphoryl or diisopropoxyphosphoryl, or represents propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, which may be substituted by substituents selected from the group consisting of fluorine- or chlorine-, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl or cyclohexylmethoxycarbonyl which may be substituted by substituents selected from the group consisting of fluorine-, chlorine-, cyano-, carboxyl-, methyl-, ethyl-, n- or i-propyl-, methoxycarbonyl- or ethoxycarbonyl-, or represents phenyl, phenyloxy, benzyl, phenylethyl, benzyloxy, phenyloxycarbonyl, benzyloxycarbonyl, oxetanyl, (in each case optionally completely or partly hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolemethyl, thiazolemethyl, pyridinylmethyl, pyrimidinylrnethyl, pyrazolylmethoxy, fliryl-methoxy or pyridylmethoxy which may be substituted by substituents selected from the group consisting of nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- or ethoxycarbonylor the radicals $R^2$ and $R^3$ together represent a substituent selected from the group consisting of

—$Q^3$—$CQ^4$—$Q^5$—, —$Q^3$—$C(R^8,R^9)$—$Q^5$—,

—$C(R^8,R^9)$—$Q^3$—$CQ^4$—, —$Q^3$—$C(R^8,R^9)$—$C(R^8,R^9)$—,

—$Q^3$—$C(R^8,R^9)$—$C(R^8,R^9)$—$Q^5$,

—$C(R^8,R^9)$—$C(R^8,R^9)$—$CQ^4$—,

—$Q^3$—$C(R^8)$=$C(R^8)$—, —$C(R^8)$=$C(R^8)$—$CQ^4$—,

—$Q^3$—$C(R^8,R^9)$—$CQ^4$—, —$N(R^{10})$—$C(R^8,R^9)$—$CQ^4$—,

—$Q^3$—$CQ^4$—$C(R^8,R^9)$—, —$Q^3$—$CQ^4$—$N(R^{10})$—,

—$Q^3$—$C(R^8,R^9)$—$CQ^4$—$N(R^{10})$—,

—$C(R^8,R^9)$—$Q^3$—$CQ^4$—$N(R^{10})$—,

—$C(R^8,R^9)$—$C(R^8,R^9)$—$N(R^{10})$—,

—$C(R^8,R^9)$—$C(R^8,R^9)$—$CQ^4$—$N(R^{10})$—,

—$C(R^8)$=$C(R^8)$—$N(R^{10})$—,

—$C(R^8)$=$C(R^8)$—$CQ^4$—$N(R^{10})$—,

—$C(R^8,R^9)$—$CQ^4$—$N(R^{10})$—,

—$N(R^{10})$—$C(R^8,R^9)$—$CQ^4$—$N(R^{10})$—,

—$C(R^8)$=$N$—$N(R^{10})$—, and

—$Q^3$—$CQ^4$—$C(R^8,R^9)$—$N(R^{10})$—, wherein $Q^3$, $Q^4$ and $Q^5$ are identical or different and in each case represent oxygen or sulphur, $R^8$ and $R^9$ are identical or different and individually represent hydrogen, fluorine, chlorine, methyl or ethyl, or together represent ethane-1,2-diyl (dimethylene), and $R^{10}$ represents hydrogen or hydroxyl, or represents methyl, ethyl, n- or i-propyl or n-, i-, s- or t-butyl which may be optionally substituted by substituents selected from the group consisting of cyano-, fluorine-, chlorine-, methoxy-, ethoxy-, acetyl-, propionyl-, methoxycarbonyl- or ethoxy-carbonyl-, or represents propenyl, butenyl, propinyl or butinyl which may be substituted by substituents selected from the group consisting of fluorine-, chorine-, or bromine, or represents cyclopropyl, cyclobutyl, cyclopentyl, cyclohexyl, cyclopropylmethyl, cyclobutylmethyl, cyclopentylmethyl or cyclohexylmethyl which may be substituted by substituents selected from the group consisting of fluorine-, chlorine-, bromine-, methyl- or ethyl-, or represents methoxy, ethoxy, n- or i-propoxy, n-, i- or s-butoxy, propenyloxy or butenyloxy which may be substituted by substituents selected from the group consisting of fluorine or chlorine, or represents benzyl or benzyloxy which may be substituted by substituents selected from the group consisting of cyano-, fluorine-, chlorine-, methyl-, ethyl-, trifluoromethyl-, methoxy-, ethoxy-, difluoromethoxy- or trifluoromethoxy-, $R^4$ represents amino, methyl, ethyl, n- or i-propyl or cyclopropyl, $R^5$ represents in each case optionally fluorine- or chlorine-substituted methyl or ethyl, $R^6$ represents hydrogen, methyl or ethyl and $R^7$ represents hydrogen, methyl, ethyl, acetyl, propionyl, methoxycarbonyl, ethoxycarbonyl, methylaminocarbonyl, ethylaminocarbonyl, dimethylaminocarbonyl, methylsulphonyl or ethylsulphonyl.

2. A process for the preparation of a diazacyclohexanedi (thi)one of the formula (I)

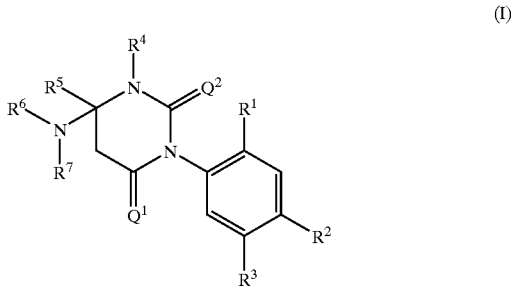

(I)

in which $Q^1$, $Q^2$, $R^1$, $R^2$, $R^3$, $R^4$, $R^5$, $R^6$ and $R^7$ have the meanings given in claim 1, which comprises reacting uracils of the formula (II)

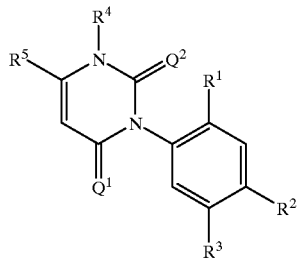

(II)

in which $Q^1$, $Q^2$, $R^1$, $R^2$, $R^3$, $R^4$ and $R^5$ have the above-mentioned meanings, with ammonia, optionally in the presence of a diluent, and, optionally reacting the compounds thus obtained of the formula (I) in which $R^6$ and $R^7$ represent hydrogen with alkylating, acylating or sulphonylating agents.

3. A method of controlling unwanted vegetation comprising administering a herbicidally effective amount of a diazacyclohexanedi(thi)one of the formula (I) according to claim 1 on such unwanted vegetation or to a locus from which it is desired to exclude such vegetation.

4. A herbicidal composition comprising a herbicidally effective amount of a diazacyclohexanedi(thi)one of the formula (I) according to claim 1 and an extender.

* * * * *